United States Patent
Caruso et al.

(10) Patent No.: US 9,370,587 B2
(45) Date of Patent: Jun. 21, 2016

(54) COLORING SUBSTANCE FOR DIAGNOSTIC OPHTALMOLOGIC USE

(71) Applicants: Ciro Caruso, Napoli NA (IT); Salvatore Troisi, Mercato San Severino SA (IT); Antonio Del Prete, Napoli NA (IT); Renato Sanseverino, Napoli NA (IT); IROS R.C. S.r.l., Napoli NA (IT)

(72) Inventors: Ciro Caruso, Napoli NA (IT); Salvatore Troisi, Mercato San Severino SA (IT)

(73) Assignees: Ciro Caruso, Napoli (NA) (IT); Salvatore Troisi, Mercato San Severino (SA) (IT); Antonio Del Prete, Napoli (NA) (IT); Renato Sanseverino, Napoli (NA) (IT); IROS R.C. S.R.L, Napoli (NA) (IT)

( * ) Notice: Subject to any disclaimer, the term of this patent is extended or adjusted under 35 U.S.C. 154(b) by 18 days.

(21) Appl. No.: 14/476,062

(22) Filed: Sep. 3, 2014

(65) Prior Publication Data

US 2014/0371569 A1 Dec. 18, 2014

Related U.S. Application Data

(63) Continuation-in-part of application No. PCT/IB2013/051635, filed on Mar. 1, 2013.

(30) Foreign Application Priority Data

Mar. 7, 2012 (IT) .............................. MI2012A0355

(51) Int. Cl.
*A61B 3/16* (2006.01)
*A61K 49/00* (2006.01)

(52) U.S. Cl.
CPC ............... *A61K 49/0021* (2013.01); *A61B 3/16* (2013.01); *A61K 49/006* (2013.01)

(58) Field of Classification Search
CPC .. A61F 9/008; A61K 31/203; A61K 49/0021; C07F 9/65618
USPC .................................................... 600/398–405
See application file for complete search history.

(56) References Cited

U.S. PATENT DOCUMENTS 2,603,632 A * 7/1952 Weidenheimer .... C07F 9/65618
544/244
5,540,227 A 7/1996 Poole
(Continued)

FOREIGN PATENT DOCUMENTS

DE 102009056597 A1 6/2011
EP 2392355 A1 12/2011
(Continued)

OTHER PUBLICATIONS

Kymionis et al, Intraocular pressure measurements after corneal collagen crosslinking with riboflavin and ultraviolet A in eyes with keratoconus, 2010, J Cataract Refract Surg, 36: p. 1724-1727.*
Wollensak et al, Riboflavin/Ultraviolet-A-induced Collagen Crosslinking for the Treatment of Keratoconus, Elsevier Inc., Vo.l 135, No. 5, p. 620-627.*

(Continued)

*Primary Examiner* — Brian Szmal
(74) *Attorney, Agent, or Firm* — Lucas & Mercanti, LLP.

(57) ABSTRACT

The present invention relates to a substance selected from the group consisting of riboflavin, its esters, salts and hydrates thereof, for use in an ophthalmic diagnostic method. In preferred aspects of the invention, the riboflavin is applied into the eye as part of a solution having a concentration from about 0.01 and 0.5% riboflavin or acceptable salt, ester, hydrate thereof.

11 Claims, 6 Drawing Sheets

(56) References Cited

U.S. PATENT DOCUMENTS

2009/0192437 A1* 7/2009 Soltz et al. ............... A61F 9/008
  604/20
2012/0121567 A1* 5/2012 Troisi et al. .......... A61K 31/203
  424/94.1

FOREIGN PATENT DOCUMENTS

WO    2006/062233  A1    6/2006
WO    2011/012557  A1    2/2011

OTHER PUBLICATIONS

Wang, UVA/Riboflavin-Induced Apoptosis in Mounse Cornea, 2008, Ophthalmologica, 222: p. 369-372.*

Martins, S. A. R., et al. : "Antimicrobial Efficacy of Riboflavin/UVA Combination (365 nm) In Vitro for Bacterial and Fungal Isolates: a Potential New Treatment for Infectious Keratitis", IOVS, vol. 49, No. 8, Aug. 2008, pp. 3402-3408; p. 3403, second paragraph, figure 2, p. 3404, first paragraph.

* cited by examiner

COLORING SUBSTANCE FOR DIAGNOSTIC OPHTALMOLOGIC USE

CROSS-REFERENCE TO RELATED APPLICATIONS

This Application is a Continuation-in-Part of PCT/IB2013/051635, filed Mar. 1, 2013, which in turn claims the benefit of priority from Italian Patent Application No. MI2012A000355, filed Mar. 7, 2012, the contents of each of which are incorporated herein by reference.

BACKGROUND OF THE INVENTION

The present invention relates to diagnostic ophthalmologic techniques and more in particular the use of riboflavin and/or its derivatives for use in such techniques.

It is well known that the measurement of intraocular pressure (IOP) is a fundamental step of ophthalmological examination routine, since the increase of its values is the major risk factor for glaucoma and one of the fundamental parameters for the diagnosis of the disease, together with the assessment of the optic disc and visual field examination. In addition, the measurement of IOP provides useful information for other eye diseases such as uveitis, and for all patients undergoing surgery on the eye, so as to be considered a routine control to be carried out in all ophthalmologic examinations.

SUMMARY OF THE INVENTION

Intraocular pressure is the result of a balance between production and outflow of aqueous humor (AH) and suffers from a number of intrinsic and extrinsic factors (heredity, race, axial length of the eyeball, age, gender, systemic blood pressure, body position, seasonal and nictemeral variations, physical activity, corneal thickness).

The measurement of intraocular pressure can be carried out with direct (manometry) or indirect (tonometry) methods. Ocular manometry is not used in clinical practice because it is more invasive, but has only limited experimental application. Instead, ocular tonometry is the most commonly used method in clinical practice. It allows indirect measurement of intraocular pressure using tools named tonometers, the principle of which is based on the relationship between intraocular pressure and the force necessary to change the natural shape of the cornea.

Tonometers actually measure the ocular tension rather than the intraocular pressure, the ocular tension depending both on the intraocular pressure and on the resistance opposed by the coating membranes. Since there is a relationship between tension and pressure, knowing the value of the former one can derive the measure of the latter. In fact, in the current clinical language, the terms intraocular pressure, intraocular pressure, eye strain are considered equivalent even if they indicate different concepts.

In the following, we will only refer to applanation tonometers, which measure the force required to flatten a constant area of the cornea or evaluate the width of the flattened area by a predetermined force, since the present invention refers to said applanation tonometers.

With the term "applanation tonometer", in the following description and in the claims, it is intended to indicate any tonometer which exploits the principle of applanation tonometry to determine the intraocular pressure.

The applanation tonometry is based on the fact that, to flatten a surface of area A of the cornea, is required an average force F acting on the surface of area A in order to balance the intraocular pressure (IOP):

IOP (Intra Ocular Pressure)=F/A

It follows that the pressure inside of an ideal sphere can be known by evaluating the width of the corneal area flattened by a constant force or by evaluating the force necessary to flatten a known corneal area. Therefore, two different types of tonometers can be used for the applanation tonometry: variable area type and variable force type.

The prototype of variable area tonometers is the Maklakov tonometer; the tonometers of Halberg, of Poster-Inglina, Barraquer, were then derived, which have had limited distribution. The best known and most used applanation tonometer in the world are those with variable force and undoubtedly the most famous thereof is the Goldmann tonometer, which is now universally used and that is the international standard for measuring IOP.

BRIEF DESCRIPTION OF THE DRAWINGS

The Goldmann technique will be better understood with reference to the following figures, wherein.

DETAILED DESCRIPTION OF THE INVENTION

Figure 1:
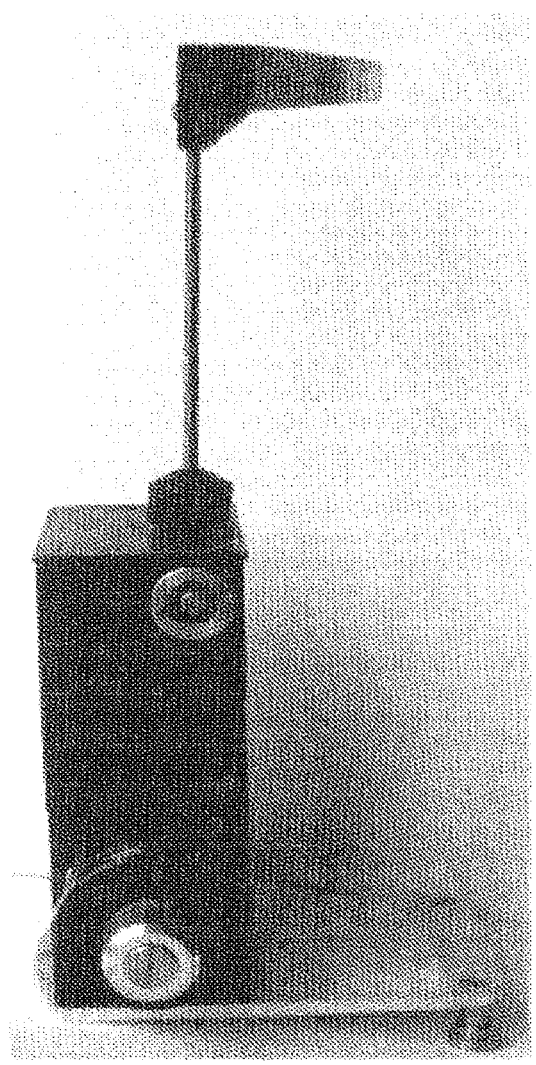
FIG. 1 shows a Goldmann tonometer.

The Goldmann tonometer, represented in FIG. 1, comprises a flattening element, consisting of a head typically made of transparent plastic and containing a prism, said head being joined to a spiral spring by means of a rod. The value of the force applied on the cornea can be varied by means of a graduated side knob, said force being expressed in grams and indicated by markings on the knob itself.

The value of the area of the flattened central cornea is 3.06 $mm^2$ and this constant value is fixed as standard reference.

Figure 2:
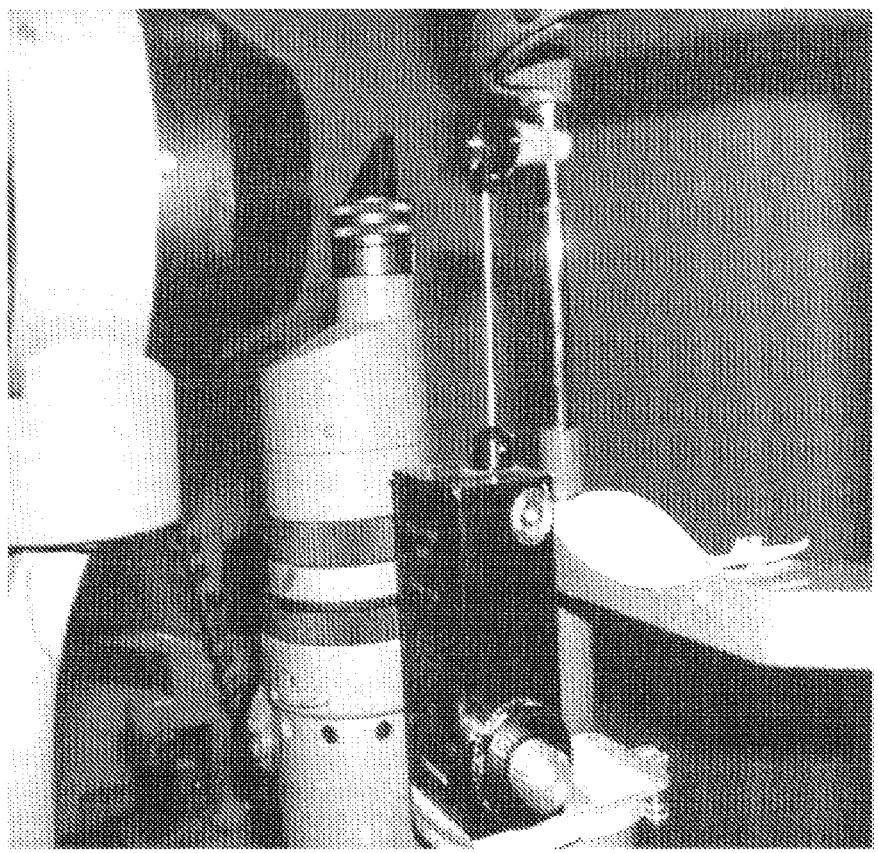
FIG. 2 shows the Goldmann tonometer of FIG. 1 mounted on a base of a slit lamp.

The examination technique provides for the support of the instrument on an appropriate basis of a slit lamp, represented in FIG. 2. After corneal anesthesia, in the lower conjunctival fornix of the patient is applied the bent end of a strip of filter paper soaked with fluorescein, fluorescent substance which serves to make more evident the edge of the flattened area by observation with blue light. As known, it is essential for a correct measurement of ocular pressure to identify with good precision the edges of the flattened area.

Figure 3:
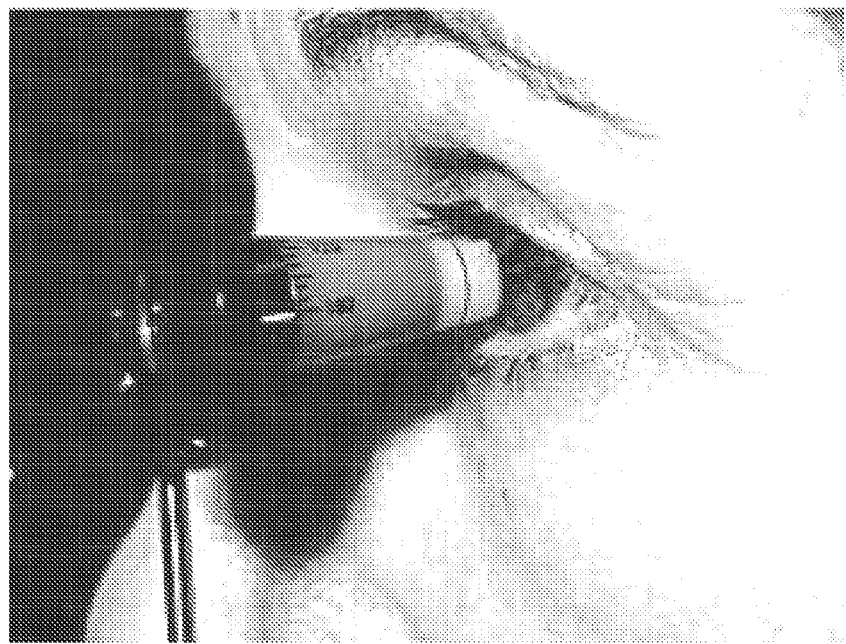
FIG. 3 shows the head of the Goldmann tonometer applied to the eye of a patient.
Figure 4:
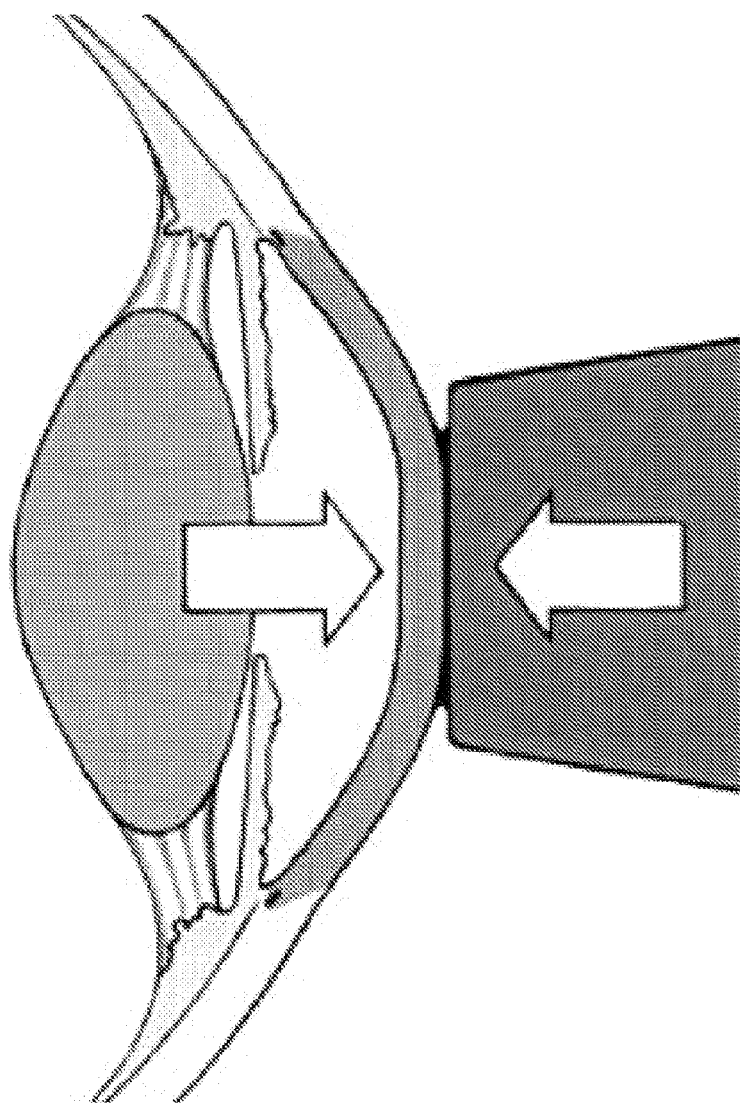
FIG. 4 illustrates the principle of measurement of intraocular pressure with the Goldmann tonometer.

The patient sits in front of the slit lamp and looks to a point of reference, as shown in FIG. 3. The lamp slit is fully opened and a cobalt blue filter is interposed to better visualize the fluorescein, namely to better visualize the edges of the flattened area. Then, a light beam is oriented so as to pass through the transparent prism and the knob is adjusted on the notch corresponding to 10 mmHg. The slit lamp is moved forward so that the prism gently enters in contact with the central part of the cornea, as in FIG. 4.

The prism, contained in the transparent plastic head, divides the circular image of the flattened corneal surface into two semicircles, that are positioned one over the other. Then through the eyepiece, two green semicircles in brilliant blue field blue can be observed.

Figure 5:
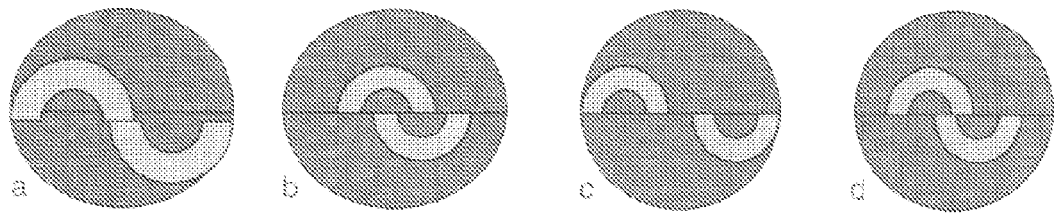
FIG. 5 shows semicircles displayed with the Goldmann tonometer in the following cases: a) excessive use of fluorescein b) excessive applanation force c) insufficient applanation force d) properly aligned semicircle.
Figure 6A:
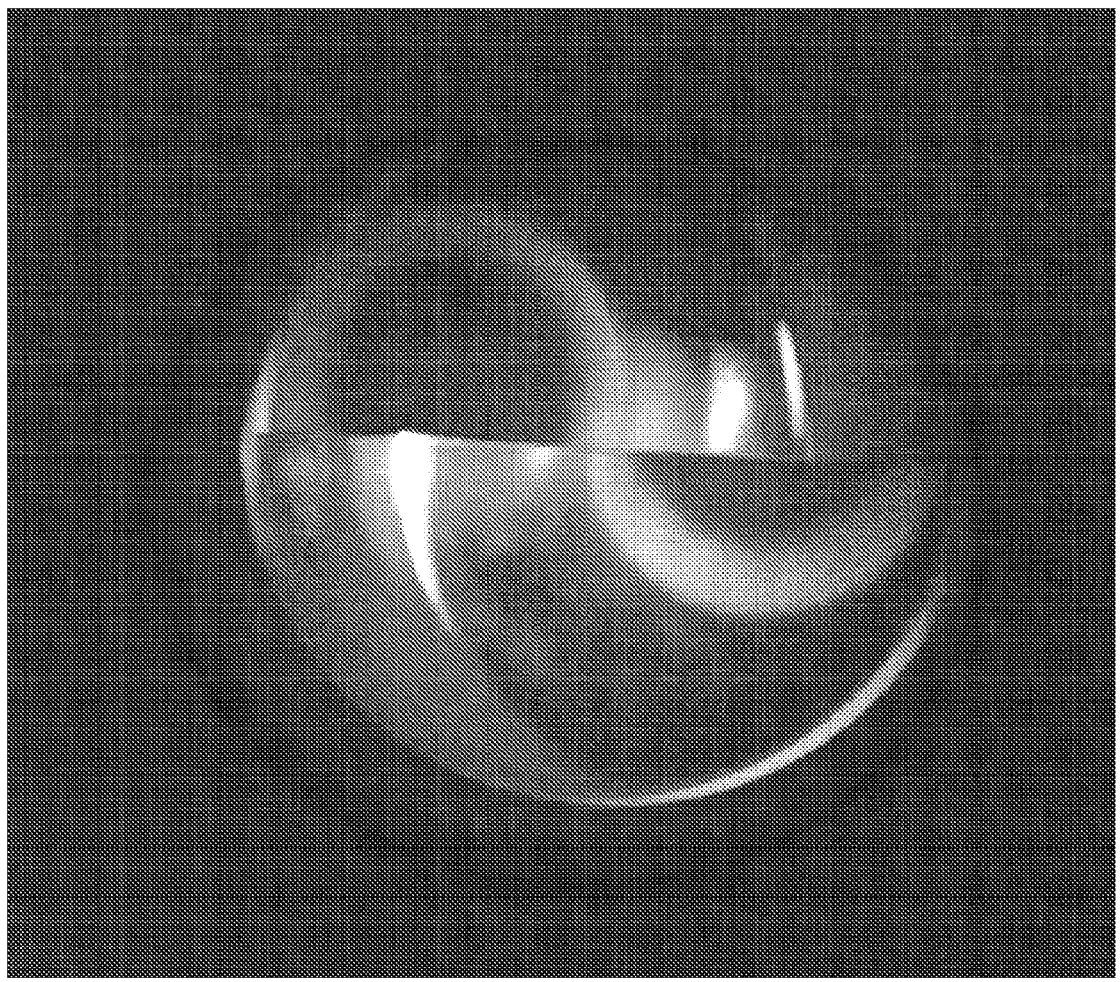
FIGS. 6a, 6b and 6c are three photographs of semicircles displayed with the Goldmann tonometer using a solution of riboflavin at a concentration of 0.1%.
Figure 6B:
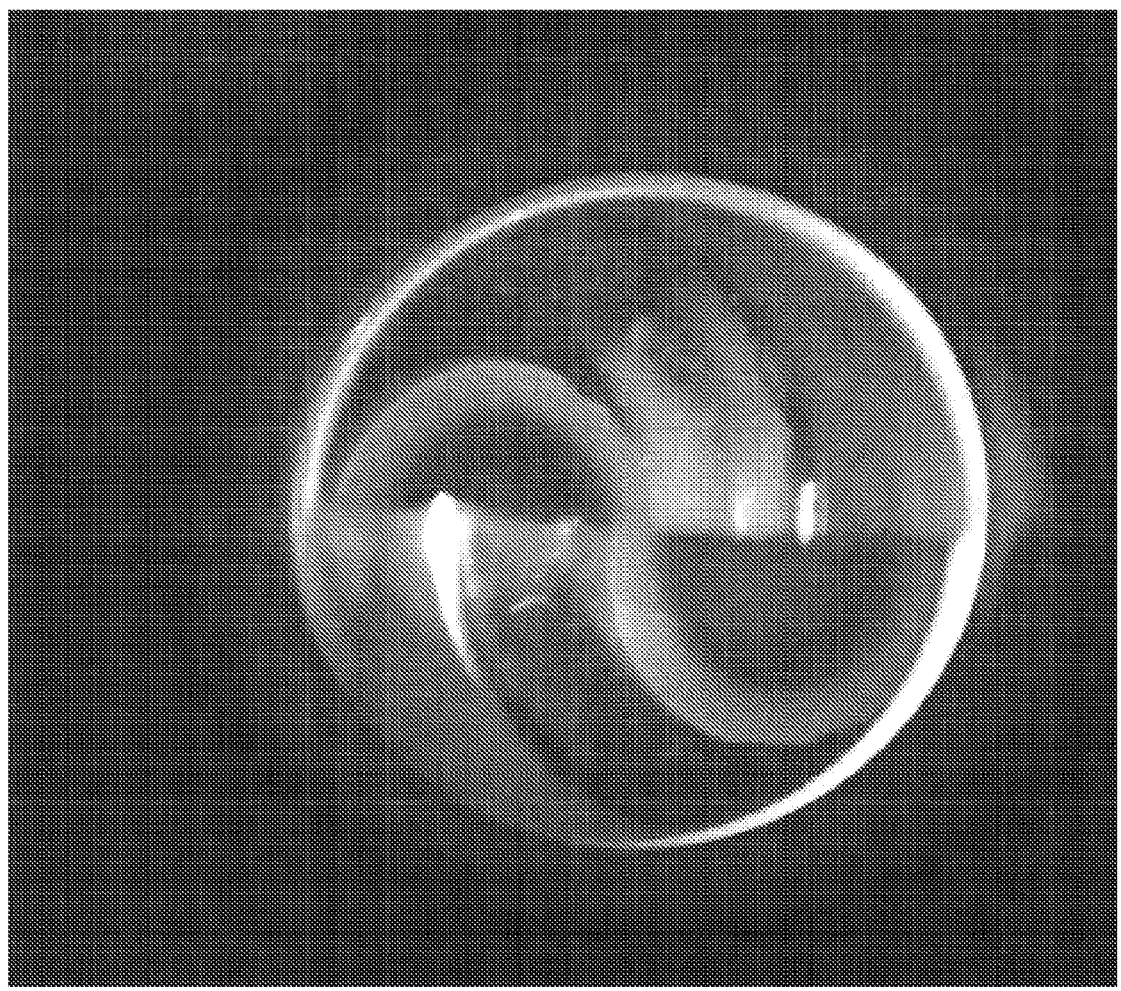
Figure 6C:
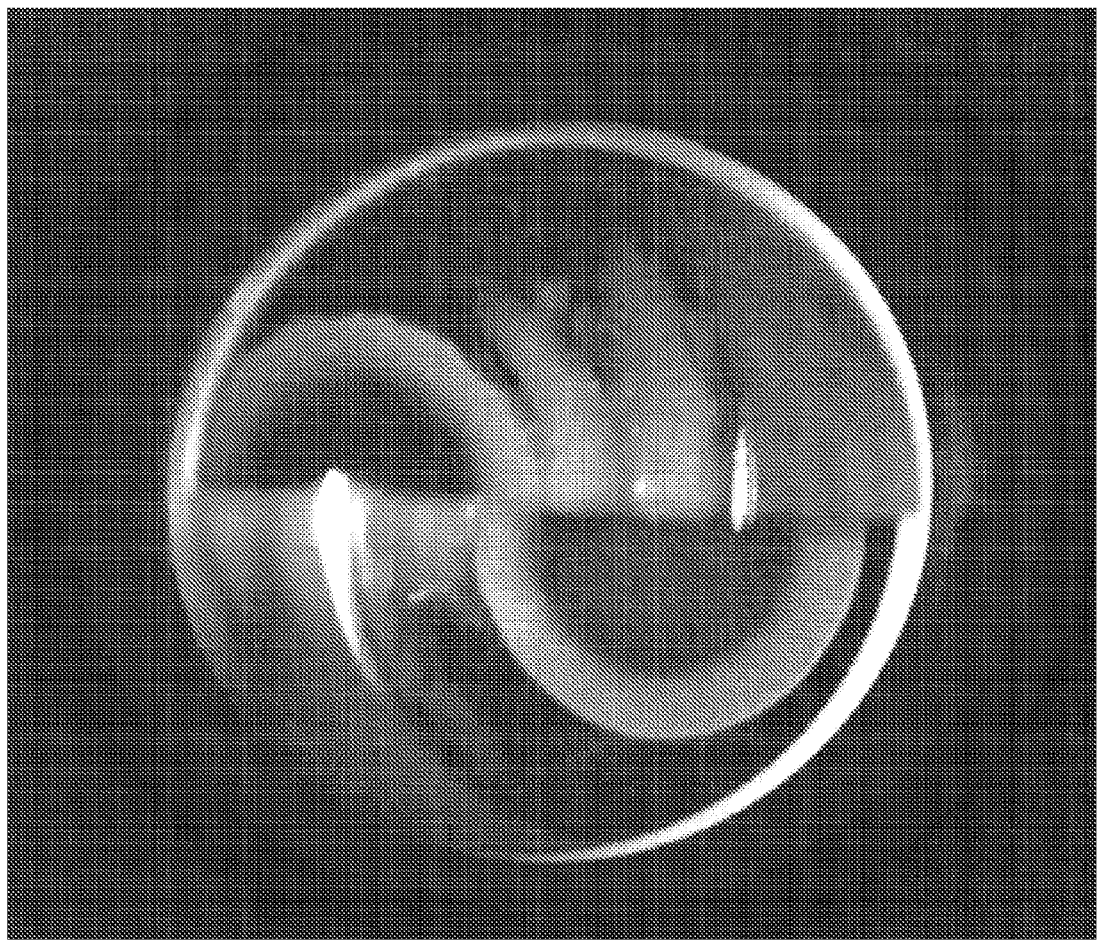

FIG. 5 shows the images obtained with the Goldmann tonometer in different cases. The side knob of the tonometer is rotated so as to bring the two semicircles in contact with their inner edge. Depending on the pressure, various aspects of the semicircles can be observed: if these are far is necessary to increase the force of applanation; if they overlap it is necessary to rotate the knob in the other direction, to decrease the exerted force. In FIG. 5A, the semicircles appear relatively thick due to an excessive use of fluorescein; in FIG. 5B the semicircles have an adequate thickness but are not correctly aligned since the applanation force excessive; in FIG. 5C the force of applanation is insufficient, in FIG. 5D the semicircle are properly aligned. The IOP is determined by multiplying the value indicated on the knob by ten.

The thickness of semicircle varies considerably depending on the amount of administered fluorescein and as an effect of alterations of the precorneal tear film.

A drawback that limits the precision of the measurement of pressure detected with this technique, consists in the fact that often the semicircles appear blurry and/or irregular, which does not allow a correct alignment thereof, and then makes the measurement imprecise and sometimes even unreliable.

Studies performed by the inventors intended to improve the accuracy of the intraocular pressure using an applanation tonometer, have led to the finding that the use of fluorescein is the main obstacle to be overcome in order to have more accurate surveys. It has been noted in fact that in some case fluorescein dirties the head of the tonometer and/or does not dissolve completely and/or does not spread uniformly in the tear film, thereby preventing a correct visualization of the semicircles.

Fluorescein is used in ophthalmologic diagnosis also to highlight any lesions on the corneal surface and to assess the state of the tear film. However, in these techniques the drawback of fluorescein consists in the poor sharpness of the image provided in the lesion and in the impossibility to detect pathological states of the deep lacrimal layers.

The object of the present invention is therefore to provide a coloring substance that can be used in ophthalmologic diagnosis and is free from said drawbacks. Said object is achieved with a substance whose main features are specified in the first claim, while other features are specified in the remaining claims.

Surprisingly, it has been found that riboflavin and its esters, as well as the salts and hydrates thereof, are not harmful to the human eye and at the same time provided with fluorescence properties and are usable in various techniques of ophthalmological diagnosis. For example, these substances are usable with an applanation tonometer, and systematically allow to obtain highly defined edges of the flattened corneal surface.

Surprisingly, it has been found also that the substances according to the present invention remain on the ocular surface about 10 times longer, compared to fluorescein.

This allows to advantageously use the substances according to the present invention also for other diagnostic purposes, such as to highlight in a more clear way an eye area surface that may be damaged for example due to corneal ulcers, infections, trauma, injury due to foreign bodies, by using the slit lamp and inserting the cobalt blue filter. In fact, the greater persistence on the lesion of the substances according to the present invention compared to fluorescein, such as in cases of corneal ulcer, allows to identify the margins of the ulcer and its depth. In this way it can be determined the intensity of inflammation in terms of extent and depth, as the margins and shape are well defined.

Riboflavin and its esters, as well as the salts and hydrates thereof, can also be used to perform tests to evaluate the state of the tear film. As is well known, the tear film is composed of three layers: an outer layer of lipid nature, an aqueous layer and a deep mucous layer. It is necessary that the tear film is in perfect condition in order that the patient feels fine.

To assess the state of the tear film, typically the BUT (break-up time) of the tear film is measured, which is a parameter indicative of the stability of the tear film. Currently, this measurement is performed by instilling a drop of fluorescein on the ocular surface and by examining the eye with a slit lamp (Wood's light cobalt blue).

Applicants have noted that fluorescein allows to evaluate only the rupture of the most superficial part of the external lipid layer, while riboflavin and its esters, salts and hydrates thereof, can also spread into the deep layer of the tear film. Consequently, by carrying out the BUT test according to the state of the art, but using a solution of riboflavin and/or its esters, salts and hydrates thereof, instead of fluorescein, allows to have information on the entire tear film and not only on the outer layer thereof.

Riboflavin and its esters, salts and hydrates thereof can also be used to conduct the so-called Turn Over and Black Line tests. The Turn Over test consists in waiting the elimination of the fluorescent substance of the tear meniscus in order to calculate the time needed by the precorneal fluids to change totally. The Black Line test consists in applying the fluorescent substance and detect a line of dark color that is visible when opening the eye after blinking. By considering the thickness of the Back Line, conclusions may be drawn about the state of the tear film. The applicants have noted that by using in these tests riboflavin and its esters, as well as the salts and hydrates thereof, instead of fluorescein, allows to obtain more precise measurements thanks to the greater permanence of the substances according to the invention on the ocular surface compared to fluorescein.

Fluorescein sodium is routinely used in ophthalmology for diagnostic purposes, for example in the diagnosis of conjunctival and corneal diseases. The dye is applied by instilling one or two drops into the conjunctival sac, or by touching the surface of the eye with a blotted paper strip containing the dye. The patient is asked to blink the eye to spread the dye over the corneal surface. After short time, a cobalt blue light is shined at the eye. Abnormalities in the corneal epithelium, such as epithelial abrasions for example, will cause the dye to stain that region that will glow green when illuminated by the blue light (Rizzuti A B: Diagnostic illumination test for keratoconus. Am J Ophthalmol 70:141, 1970; Berliner M L: Biomicroscopy of the eye. New York, Paul D. Hoeber, 1943; Soper J W, Sampson W G, Girard L J: Corneal topography, keratometry, and contact lenses. Arch. Ophthalmol. 66:753, 1962), the contents of each of which are incorporated herein by reference.

The inventors have discovered unsuspected properties of the claimed substances that make them particularly adapted to be used in ophthalmic diagnostic tests in place of fluorescein. Riboflavin is not tinged with the cells, but tinged with the tear film; it makes visible the tear film, which in physiological condition is transparent. Riboflavin is hydrophilic and does not penetrate into the cells, but if the junctions between epithelial cells (gap-junction) are disrupted, the stained tear film is deposited in the intercellular spaces, and it colors the affected area of the cornea, when it is illuminated by cobalt blue light.

Riboflavin as a dye is applied by instilling one or two drops of solution of riboflavin (for example riboflavin 5-phosphate) into the conjunctival sac, or by touching the surface of the eye with a blotted paper strip containing riboflavin. The excess of riboflavincan be removed or washed by tears. In the same manner, riboflavin 5-phosphate can be used in all cases of corneal diseases characterized by corneal ulcers and/or corneal epithelial erosion.

For topical use, riboflavin is available in solution. Since the solutions of the dyes are susceptible to contamination by microorganisms, are available as single-dose formulations without preservatives. The topical use of riboflavin is associated with side no effects.

To stain the tear film with riboflavin, instill one or two drops of solution into the conjunctival sac, when epithelial damage is suspected; this happens as a result of a: corneal or conjunctival trauma, removal of contact lenses, removal of a foreign body.

Local administration of riboflavin may also be indicated to highlight the exact measure and the positioning of the contact lenses, rigid gas-permeable, for the execution of the Seidel test, for evaluation of the functionality of lacrimal assay (Johnson) and stability of the tear film (tear film break-up time).

The stability of the tear film (tear film break-up time) is commonly assessed through the following procedure. The patient is seated at the slit lamp and then he rests his chin on the chin-rest of the instrument. Patient is asked to keep his eyes open long enough without blinking or the doctor can keep the eyelids open with his fingers and prevent a blink of the eyelids: from this moment the doctor measures the time in which the tear film will begin its rupture. In dry eye patients, the tear film is unstable, and breaks down more quickly. The breakup time (BUT) of the tear film after staining with riboflavin is a key indicator of the stability of the tear and one of the most simple clinical tests for the diagnosis of lacrimal dysfunction syndrome. The result of the BUT is measured using the technique originally postulated by Norn and later by Lemp and Holly. These authors then carried out the BUT with fluorescein and measured the time elapsed between the last complete blink and the appearance of the first area of tear film break at the level of the ocular surface, through the use of a slit lamp with a cobalt blue light. In order to establish the degree of severity of the disease, a simple test such as the breakup time allows to quantify the degree of instability of the tear film as normal, less than or equal to 10 seconds, less than or equal to 5 seconds.

There are three commonly used methods to grade ocular surface staining: the van Bijsterveld system (van Bijsterveld OP:Diagnostic tests in the sicca syndrome. Arch Ophthalmol. 82:10-14 1969), the NEI/Industry Workshop guidelines (Lemp MA: Report of the National Eye Institute/Industry Workshop on clinical trials in dry eyes. CLAO J. 21:221-232 1995), and the Oxford Scheme (Bron A J, Evans V E, Smith J A: Grading of corneal and conjunctival staining in the context of other dry eye tests. Cornea.22:640-650 2003)

The van Bijsterveld system uses a scale for evaluating the degree of staining intensity measured using a scale from 0 to 3 points in 3 areas: conjunctiva nasal, temporal conjunctiva and cornea. The maximum score obtainable with this system is equal to 9.

The Oxford system and the NEI Workshop system using a rating with wider intervals, allowing identification of minor variations in the condition of the ocular surface.

The goal of the BUT test is to measure the time interval between the last complete blink eyelid and tear film breakup of the first beat of the next full eyelid. This test may be carried out using riboflavin in place of fluorescein by:

instilling a sufficient amount of riboflavin as part of a ophthamologically acceptable solution as described herein, in the lower conjuntival sac;
asking the patient to blink several times;
measuring the time between the last blink and the first appearance of a dark spot on the cornea (the formation of a dry zone) on the tear film.

A tear film breakup time of less than 10 seconds suggests a dry eye.

Use of riboflavin in ophthalmic diagnostic test is particularly convenient because of the good bio-availability of riboflavin, for the absence of toxic effects on the corneal epithelium, for the very fast speed of diffusion on the surface of the eye and of the short duration of its effect. Riboflavin penetrates the intercellular spaces between the corneal epithelial cells and the impregnation of the dye indicates rupture of intercellular junctions.

In clinical diagnostic practice, riboflavin and its esters, as well as salts and hydrates thereof can be used according to the present invention to check the protective quality of the tear film, to check the integrity of ocular surfaces, to check if ocular structures are watertight, such as in case of cataract, glaucoma, reparation of ocular wounds, to check the proper fitting of rigid and gas permeable contact lenses, and to follow up the contact lenses fitting. In other words, the substance according to the present invention can be used for diagnostic purposes such as for example detection of abnormal tear production (dry eye), short breaks in the tear film (measurements of break up time), tear meniscus thinner than normal, blocked tear ducts, loss of integrity of conjunctiva and/or cornea, injury, trauma, infection, abrasion, epithelial erosions, punctuate superficial keratitis, ulcers, corneal oedema, infectious keratitis (herpetic, acantamoeba), ocular sutures that are not watertight (Seidel sign), foreign bodies, such as metal, glass, stone, eyelashes or dust in anterior ocular surface, foreign bodies on, or plugged in, the tarsus and/or in the cornea.

The greater permanence of the substances according to the invention compared to fluorescein, make these substances suitable to appreciate more slowly and with greater precision the contact between a contact lens and the cornea. Otherwise, the fluorescein, being more fluid, creates smears and is more readily removed, sometimes without satisfactorily define the margins of the contact lens.

According to the present invention, there is thus provided a new substance for diagnostic use in ophthalmology, such as in the measurement of intraocular pressure with an applanation tonometer, consisting of riboflavin and/or its esters, and/or of the salts and hydrates thereof. Among the esters of riboflavin is preferably used riboflavin 5-phosphate.

Among salts and hydrates of said esters, mention can be made of riboflavin 5-phosphate ester sodium salt, and riboflavin 5-phosphate sodium salt hydrate of the following formula:

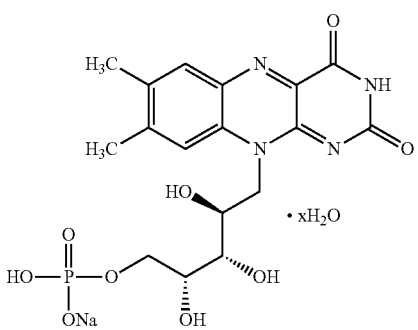

Preferably, for diagnostic purposes measurement of the intraocular pressure, a solution of riboflavin and/or its esters, and/or salts and/or hydrates thereof, such as riboflavin-5-phosphate is used, in a concentration between 0.01% and 0.5%, more preferably between 0.1% and 0.4%, even more preferably between 0.25% and 0.35%. A preferred concentration is for example 0.3%. In the present description and in the claims, the percentage concentrations are to be understood as g/100 ml.

For other diagnostic purposes, a solution of riboflavin and/or its esters, salts and hydrates thereof such as riboflavin-5-phosphate, in a concentration between 0.08% and 0.3% is preferably used.

According to a further aspect, the invention relates to an applicator of riboflavin and/or its esters, salts and hydrates thereof, which consists in a strip of filter paper with a head soaked with riboflavin and/or its esters, salts and hydrates, of the type currently used to apply the fluorescein on corneal surface when pressure is measured with an applanation tonometer.

According to a further aspect, the invention relates to a process for the measurement of intraocular pressure, comprising the steps of:

a) administration of a sufficient amount of an aqueous solution of riboflavin and/or its esters, salts and hydrates in an eye of a patient;

b) detection of intraocular pressure by use of a applanation tonometer.

In most embodiments, instilling one, two or several drops of a riboflavin solution as described herein will be a sufficient amount for carrying out any of the methods described herein.

DESCRIPTION OF EXEMPLARY EMBODIMENTS

In the remainder of this description, reference is made to riboflavin and to the Goldmann tonometer, but it applies mutatis mutandis also to other substances according to the invention and to any other applanation tonometer, as the tonometers of Maklakov, of Halberg of Poster-Inglina or Barraquer.

In all tests, carried out by the inventors with a Goldmann tonometer, using riboflavin instead of fluorescein, were shown surprisingly regular circular semicircles, with edges of constant thickness and substantially free of smears, which have enabled a highly precise and repeatable measurement of the intraocular pressure.

The substances according to the invention are definitely not harmful to the human eye that do not cause side effects which sometimes were recorded for fluorescein. They have a typical yellow color that allows to see the edges of the flattened cornea through the cobalt blue filter of any Goldmann tonometer. Consequently, it is possible to use the substance according to the invention without having to modify the Goldmann tonometers of currently available.

Without wishing to limit the invention to a theory, the inventors believe that the excellent sharpness of semicircles displayed using the substances according to the invention can be explained by the fact that said substances spreads easily and uniformly in the tear film and do not dirty the head of the Goldmann tonometer, which is placed in contact with the cornea.

It is noted that the thickness of the semicircles varies relatively little as a function of the substance administered, so that it is possible to use solutions of said substances with concentrations 10 times higher, and still obtain highly accurate measurements. As well as for fluorescein, the greater the amount of riboflavin applied, the greater will be the thickness of displayed semicircles. However, unlike fluorescein, even in the case of an "excessive" use of the substances according to the present invention, the semicircle will be well defined thus allowing proper detection of the intraocular pressure.

Preferably, an aqueous solution of the substance according to the present invention with a concentration of at least 0.01% will be used, in order to have semicircles with a minimum thickness that allows easy viewing. Tests carried out with high concentration aqueous solutions of riboflavin (0.5%) produced relatively thick but well-defined semicircles, which have resulted in a sufficiently precise measurement of eye pressure.

Good results have been obtained with an aqueous solution of the substance according to the present invention with concentration between 0.03% and 0.3%.

At the preferred concentrations, only one drop of solution of the substance according to the present invention is enough for measuring the intra-ocular pressure.

Preferably, the solution of the substance according to the present invention will be distributed in disposable containers.

It is however possible to realize applicators of the substance according to the present invention similar to those currently used for fluorescein. They will consist of a strip of filter paper for use ophthalmological equipped with a portion, for example one end, soaked with the substance according to the present invention.

Example 1

Three patients were subjected twice to measurement of the intra-ocular pressure, in order to verify the reliability of the use of riboflavin in the measurement of intraocular pressure with an applanation tonometer. One drop of a solution of riboflavin 0.3% was administered to each patient, after installation of anesthetic eye drop (oxybuprocaine hydrochloride 0.2%). Subsequently, the intraocular pressure was measured with Goldmann tonometer. Then, 15 minutes after eyewash with saline solution (NaCl 0.9%), a new measurement was carried out for comparison purposes with the same method but using a standard staining with fluorescein strips (Haag Streit).

The patient data and the results of the measurements are shown below:

1) patient M.T., male, 82 years, eye tone usually within the limits.

Measurement with riboflavin: r.e. (right eye): 17 mm Hg, l.e. (left eye): 16 mmHg.

Measurement with fluorescein: r.e.: 17 mmHg, l.e.: 16 mmHg (average of three measurements)

2) patient G.D.L., female, aged 28, suffering from chronic open-angle glaucoma, in pressure balance therapeutic.

Measure with riboflavin: r.e. 18 mmHg, l.e. 18 mmHg.
Measure with fluorescein: r.e.: 18 mmHg, l.e.: 18 mmHg.
3) Patient A.S., female, aged 46, recently found hypertonic
Measure with riboflavin: r.e.: 24 mmHg, l.e.: 25 mmHg.
Measure with fluorescein: r.e.: 24 mmHg, l.e.: 24.7 mmHg.

As it is shown, the measures of the values obtained in millimeters of mercury, carried out using a solution of riboflavin, are substantially identical and/or superimposable to those obtained using the fluorescein, but with a better performance both in terms of sharpness, and of image of the semicircles that do not appear as smeared. Furthermore, a better cleaning is detectable of the flattening element of the tonometer, which after the measurement is not contaminated by residues of riboflavin, as instead happens in the case of the use of fluorescein.

What we claim is:

1. A process for the measurement of intraocular pressure in a patient, comprising:
   a) administering an aqueous solution containing riboflavin and/or its esters, salts and hydrates to an eye of a patient in an amount sufficient to permit detection of intraocular pressure of the eye with an applanation tonometer; and
   b) detecting the intraocular pressure in the eye into which said aqueous solution was administered using an applanation tonometer based on the amount of riboflavin present on the cornea of said eye.

2. The process according to claim 1, wherein the riboflavin esters, salts and hydrates in the aqueous solution are selected from the group consisting of riboflavin 5'-phosphate ester, riboflavin 5'-phosphate ester sodium salt, and riboflavin 5' ester sodium salt hydrates.

3. The process according to claim 1, wherein the aqueous solution contains riboflavin.

4. The process according to claim 1, wherein the concentration of the riboflavin and/or its esters, salts and hydrates in the aqueous solution is from 0.01% to 0.5%.

5. The process according to claim 4, wherein the concentration of the riboflavin and/or its esters, salts and hydrates in the aqueous solution is from 0.1% to 0.4%.

6. The process according to claim 5, wherein the concentration of the riboflavin and/or its esters, salts and hydrates in the aqueous solution is from 0.25% to 0.35%.

7. The process according to claim 1, wherein the riboflavin in the solution is riboflavin-5-phosphate.

8. The process according to claim 7, wherein the concentration of the riboflavin-5-phosphate in the solution is between 0.01% and 0.5%.

9. The process according to claim 7, wherein the concentration of the riboflavin-5-phosphate in the solution is between 0.1% and 0.4%.

10. The process according to claim 7, wherein the concentration of the riboflavin-5-phosphate in the solution is between 0.25% and 0.35%.

11. The process according to claim 7, wherein the concentration of the riboflavin-5-phosphate in the solution is 0.3%.

* * * * *